United States Patent [19]

Evans et al.

[11] 4,302,612

[45] Nov. 24, 1981

[54] SYNTHESIS OF PERFLUORODIALDEHYDES

[75] Inventors: David H. Evans; Richard B. Greenwald, both of Cambridge, Mass.

[73] Assignee: Polaroid Corporation, Cambridge, Mass.

[21] Appl. No.: 872,614

[22] Filed: Jan. 26, 1978

Related U.S. Application Data

[60] Division of Ser. No. 705,411, Jul. 15, 1976, abandoned, which is a continuation-in-part of Ser. No. 595,489, Jul. 14, 1975, abandoned.

[51] Int. Cl.³ .................... C07C 43/12; C07C 41/01; C07C 29/00
[52] U.S. Cl. .................................. 568/604; 568/812
[58] Field of Search ............ 260/601 R, 601 H, 345.9, 260/615 A

[56] References Cited

U.S. PATENT DOCUMENTS

| | | | |
|---|---|---|---|
| 2,931,937 | 4/1960 | Stansbury et al. | 260/615 |
| 3,255,229 | 6/1966 | Hauptschen | 260/601 H |
| 3,344,193 | 9/1967 | Carr | 260/601 H |
| 3,360,568 | 12/1967 | Hauptschen | 260/601 H |

OTHER PUBLICATIONS

Pierce et al., "J. Amer. Chem. Soc." vol. 76, pp. 300–301.
Husted et al., "J. Amer. Chem. Soc." vol. 74, pp. 5422–5426.
Braid et al., "J. Amer. Chem. Soc." vol. 76, p. 4027.

*Primary Examiner*—Werren B. Lone
*Attorney, Agent, or Firm*—Sybil A. Campbell

[57] ABSTRACT

This invention is concerned with the synthesis of perfluorodialdehydes from the corresponding perfluorodiesters and with intermediates useful in the preparation of the perfluorodialdehydes.

9 Claims, No Drawings

SYNTHESIS OF PERFLUORODIALDEHYDES

CROSS-REFERENCE TO RELATED PATENT APPLICATIONS

This application is a division of copending application Ser. No. 705,411 filed July 15, 1976, now abandoned, which is a continuation-in-part of application Ser. No. 595,489 filed July 14, 1975, now abandoned.

BACKGROUND OF THE INVENTION

1. Field of the Invention

This invention relates to a novel method of synthesizing perfluorodialdehydes and to novel intermediates useful in the synthesis thereof.

2. Description of the Prior Art

Though various procedures have been proposed for synthesizing aldehydes, in general, they have not always been successful when applied to highly fluorinated compounds because of the relatively inert nature of fluorinated compounds as compared to their hydrocarbon counterparts. Usually, the synthesis of perfluoromonoaldehydes has been accomplished by the lithium aluminum hydride reduction of the corresponding esters at low temperatures as described by D. R. Husted and A. H. Ahlbrecht, J. Amer. Soc., 74, p. 5422 (1952). Inverse addition has been reported to improve yields as discussed by O. R. Pierce and T. G. Kane, ibid., 76, p. 300 (1954) and by M. Braid, H. Iserson and F. E. Lawlor, ibid., 76, p. 4027 (1954).

Although we anticipated no difficulty in the preparation of perfluorodialdehydes by the standard methods used for the perfluoromonoaldehydes, only traces of the desired product could be detected from the lithium aluminum hydride reduction of dimethyl perfluoroadipate in ether at either 0° C. or −70° C. Equally unsuccessful was the attempted reduction of perfluoroadipoyl chloride in tetrahydrofuran using lithium tri-t-butoxyaluminum hydride.

U.S. Pat. No. 3,344,193 discloses the use of catalytic reduction in the preparation of perfluorinated dialdehydes, such as, 2,2,3,3,4,4-hexafluoro-1,5-pentanedialdehyde. As described therein, the fluorinated dialdehydes are synthesized from the corresponding diacid halides by catalytic reduction preferably using a palladium on carbon catalyst and particularly a poisoned catalyst of this type.

In one aspect, the present invention is concerned with a method of preparing perfluorodialdehydes. In another aspect, the present invention is concerned with intermediates useful in the production of perfluorodialdehydes and the preparation of the intermediates.

SUMMARY OF THE INVENTION

It is one object of the present invention to provide a method of synthesizing perfluorodialdehydes.

It is another object of the present invention to provide intermediates useful in the preparation of said perfluorodialdehydes.

It is a further object of the present invention to provide a method for preparing said intermediates.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

According to the present invention, it has been found that perfluorodialdehydes may be prepared by chemical reduction by employing a certain reducing agent in certain amounts at reduced temperatures. As compared to standard chemical reductions and to the catalytic reduction previously employed in the preparation of perfluorodialdehydes, the subject method affords greater reaction control in obtaining the dialdehyde product, greater ease of isolation of the product and greatly improved yields. For example, yields of over 50% by weight of highly pure product are obtained with the subject method as compared to negligible yields for standard chemical reductions and yields of less than 50% by weight crude product as obtained in the catalytic reduction mentioned above.

For a fuller understanding of the nature and objects of the invention, reference should be had to the following detailed description.

DESCRIPTION OF THE PREFERRED EMBODIMENTS

Specifically, it has been found that perfluorodialdehydes may be prepared through the intermediate obtained upon reduction of the corresponding perfluorodiesters employing sodium bis-(methoxyethoxy)-aluminum hydride (Vitride) at temperatures below about −40° C. Where the perfluorodiester starting material contains less than 4 perfluoromethylene groups, the intermediate obtained is a cyclic hemi-acetal, and where the diester starting material contains 4 or more perfluoromethylene groups, the intermediate obtained is a linear dihydrate as shown in the following reaction sequence wherein R represents alkyl, preferably lower alkyl and x represents 2 to 12.

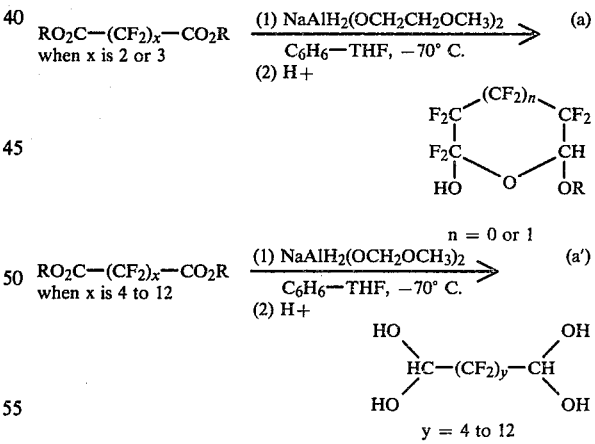

As an illustration, when dimethyl perfluoroadipate was treated with Vitride under the conditions discussed above, 2,2,3,3,4,4,5,5-octafluoro-1,6-hexanedialdehyde dihydrate was obtained which upon dehydration with phosphorus pentoxide yielded the corresponding free dialdehyde. When diethyl perfluoroglutarate was reduced under the same conditions, 2-ethoxy-6-hydroxy-3,3,4,4,5,5-hexafluoropyran was obtained which may be treated with acid to open the ring and then dehydrated with phosphorus pentoxide to yield the corresponding dialdehyde. The formation of the cyclic hemi-acetal seems best explained by intramolecular cyclization of the initial reduction product where a 5- or 6-membered ring can form followed by further reduction as illustrated below.

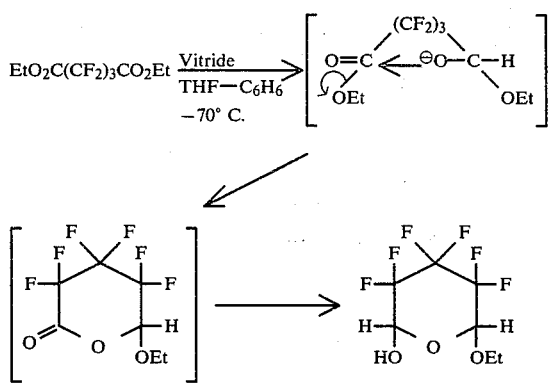

Where the initial reduction product cannot form a 5- or 6-membered ring, the linear dihydrate is formed.

The novel intermediates of the present invention may be represented by the formulas:

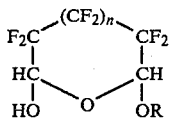 (Ia)

wherein n is an integer 0 or 1 and R represents alkyl, preferably lower alkyl having 1 to 4 carbon atoms, such as, methyl, ethyl, propyl, isopropyl, n-butyl and s-butyl; and

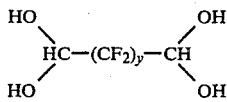 (Ib)

wherein y is a positive integer from 4 to 12.

The perfluorodialdehydes that are obtained from these intermediates may be represented by the formula:

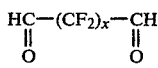 (II)

wherein x is a positive integer from 2 to 12.

Both the linear dihydrate and cyclic hemi-acetal intermediates of Formulas Ia and Ib and also, the free dialdehydes of Formula II may be reacted with 2,4-dinitrophenylhydrazine to yield the corresponding bis-α,ω-hydrazones having the formula

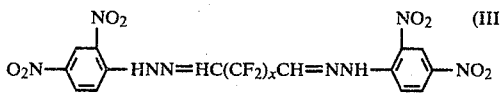 (III)

wherein x has the same meaning given above.

The dialdehydes also undergo reaction with diazomethane to give the corresponding diepoxides having the formula

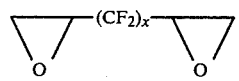 (IV)

wherein x has the same meaning given above and the dialdehydes also undergo a Wittig reaction to yield the corresponding diolefins having the formula R'HC=HC(CF$_2$)$_x$CH=CHR' (V)

wherein R' represents hydrogen, alkyl, preferably lower alkyl having 1 to 4 carbon atoms and —CO$_2$R" wherein R" represents alkyl, preferably lower alkyl having 1 to 4 carbon atoms.

The dihydrates of Formula Ib when treated with hydrochloric acid in alkanol afford the hemi-acetals having the formula

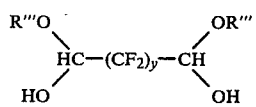 (VI)

wherein R''' is alkyl, preferably lower alkyl having 1 to 4 carbon atoms and y has the same meaning given above.

For convenience, the dialdehydes of Formula II and the derivatives thereof as set out in Formulas III to V may be represented by the following formula Z(CF$_2$)$_x$Z (A)

wherein Z is selected from —CHO,

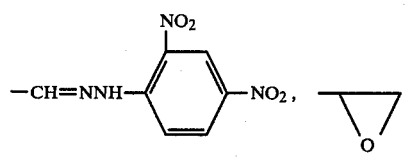

and —CH=CHR' wherein R' has the same meaning given in Formula V.

The intermediate of formula Ia and the derivatives thereof as shown in formula VI may be represented by the formula

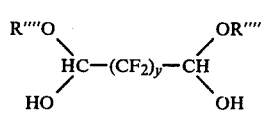

wherein R'''' is hydrogen or alkyl, preferably lower alkyl having 1 to 4 carbon atoms and y has the same meaning given above.

The perfluorodiester starting materials are known and usually are prepared by reacting a perfluoro acid, for example, (CF$_2$)$_x$(COOH)$_2$ wherein x is 2 to 12 with ROH to yield the corresponding diester, (CF$_2$)$_x$(COOR)$_2$.

As noted above, the method of the present invention is carried out under certain conditions using a particular reducing agent. The perfluorodiesters are reduced with sodium bis-(2-methoxyethoxy)aluminum hydride (Vitride) in an organic solvent or mixture of organic solvents at a temperature of less than about −40° C. and usually at a temperature between about −60° to −70° C. At higher temperatures, for example, room temperature, the reaction of perfluorodiesters with Vitride gives perfluorodiols especially where a substantial excess of Vitride is employed, for example, 2 to 2.5 equivalents of Vitride per equivalent of diester. In the subject method of synthesizing the dialdehydes, the Vitride is employed in amounts ranging from 1 to 1.5 equivalents per equivalent of diester which together with the low reaction temperature is essential for obtaining the desired intermediate so that upon dehydration the dialdehyde product will be obtained in good yields.

Since the Vitride reducing agent is commercially available as a 70% solution in either benzene or toluene, it is convenient to use the reducing agent as the 70% solution and employ a solvent having a freezing point such that it will be liquid at the selected reaction temperature. Usually the solvent has a freezing point or freezing range below about −40° C. and preferably below about −60° C. Suitable solvents include ethers, particularly alkyl ethers either open-chain or cyclic, such as, ethylene glycol dimethyl ether, tert-butyl ethyl ether, butyl methyl ether, cyclohexyl methyl ether, di-n-propyl ether, diethyl ether, dimethyl ether and tetrahydrofuran. Preferably, tetrahydrofuran is employed with the benzene or toluene solution of the reducing agent. The quantity of solvent is not critical and is used in amounts to provide a fluid reaction mixture which is readily determined empirically.

After the reduction is complete, any excess of Vitride remaining is decomposed by adding chilled aqueous 20% sulfuric acid to the reaction mixture and permitting the temperature to rise slightly, i.e., about 10 to 20 degrees. The intermediate obtained whether a cyclic hemi-acetal or a linear dihydrate is isolated and dried before dehydration to the dialdehyde.

When the reduction affords a cyclic hemi-acetal intermediate, the dialdehyde may be obtained by dissolving the compound in a mixture of ethanol-15% HCl, refluxing for about one hour, evaporating to dryness under reduced pressure, azeotroping with benzene to effect drying and then treating the residue with a dehydrating agent in an inert anhydrous organic solvent. For example, the dehydration reaction is conveniently carried out using phosphorus pentoxide as the preferred dehydrating agent in an amount of 2 to 3 equivalents per equivalent of intermediate in an inert anhydrous organic solvent having a boiling higher than the product such that substantially all of the product will boil out first. Preferably, the solvent is diphenyl ether.

When the reduction affords a linear dihydrate intermediate, the dihydrate may be directly dehydrated to the free dialdehyde without being treated with acid.

The following examples are given to further illustrate the present invention and are not intended to limit the scope thereof.

EXAMPLE 1

Preparation of 2,2,3,3,4,4,5,5-octafluoro-1,6-hexanedialdehyde dihydrate:

In a 3 liter three neck round bottom flask fitted with a mechanical stirrer, dropping funnel equipped with a drying tube, and low temperature thermometer was placed a solution of 50.0 g. (0.158 mol) of dimethyl perfluoroadipate in 450 ml. of dry tetrahydrofuran (THF). The reaction mixture was cooled to −70° C. (dry ice-acetone) and 67.5 ml. (0.238 mol.) of Vitride (70% in benzene) diluted with 50 ml. of THF was added dropwise over 30 min. with vigorous stirring. The temperature of the reaction was maintained at ≦−70° C. during the addition and at −70° C. for 2.5 hours after addition was complete. To the viscous mixture 500 ml. of 20% sulfuric acid previously chilled at 5° C. was added dropwise. The temperature of the reaction was allowed to rise to −50° C. and maintained until the excess Vitride had been decomposed. The mixture was then allowed to warm spontaneously to room temperature. Ether (400–600 ml.) was added with vigorous stirring until a homogeneous two-phase system was obtained. The layers were separated and the aqueous phase extracted with an additional 200–300 ml. of ether. The combined ether extracts were washed to neutrality with brine, dried over MgSO$_4$, and evaporated under reduced pressure. The title compound was left as a thick syrup, 45.2 g. (96% by weight), $\nu_{max}^{neat}$ 3600–2000 (bd) cm$^{-1}$.

EXAMPLE 2

Preparation of 2,2,3,3,4,4,5,5-octafluoro-1,6-hexanedialdehyde:

The dialdehyde dihydrate, 45.2 g., prepared in Example 1 above was stirred with 3 molar equivalents of phosphorous pentoxide in 60 ml. of diphenyl ether* for 10 min. and then the mixture was distilled through a 60 mm Vigreaux column taking care to exclude moisture. The material so collected (28.1 g.) was redistilled to give 26.5 g. (65% by weight) of the title compound as a colorless liquid: boiling range 122°–23° C., $\eta_D^{26}$ 1.3170 $\nu_{max}^{neat}$ 2900, 2850 (sh), 1765 cm$^{-1}$; nmr (CDCl$_3$) δ 9.47 (m).

*Previously dried by heating over phosphorous pentoxide so that no materials of bp <160° remained. Decantation of the clear supernatant from the dark residue was found to be satisfactory.

EXAMPLE 3

Preparation of 2,2,3,3,4,4,5,5-octafluoro-1,6-diethoxy-1,6-hexanediol:

A solution of 5.0 g. (0.017 mol.) of 2,2,3,3,4,4,5,5-octafluoro-1,6-hexanedialdehyde dihydrate in 25 ml. of abs. ethanol was saturated with HCl and allowed to remain overnight at room temperature. The precipitate was collected and washed with benzene to give 5.6 g. (84% by weight) of the title compound: melting range 110°–111° C.; nmr (DMSO-d$_6$), δ 1.10 (t,3H,J=6.5 Hz), 3.24–3.90 (m, 2H), 4.94 (t,1H,J=11 Hz), 7.34 (bd.s,1H, exch.).

EXAMPLE 4

Preparation of 2-ethoxy-6-hydroxy-3,3,4,4,5,5-hexafluoropyran:

A solution of 30.3 g. (0.015 mol.) of Vitride (70% in benzene) in 30 ml. of dry tetrahydrofuran (THF) was added dropwise over 45 min. to a stirred solution of 25.0 g. (0.084 mol.) of diethyl perfluoroglutarate in 200 ml. of THF at −70° C. The mixture was stirred for an additional 2 hours at −70° C. followed by decomposing the Vitride as described in Example 1 to give 16.8 g. (87% by weight) of the title compound as a pale yellow liquid. Distillation afforded a colorless oil: boiling range 65°–70° C. (1.7 mm); n$_D^{26}$ 1.3671; $\nu_{max}^{neat}$ 3350 (broad) cm$^{-1}$; nmr (CDCl$_3$) δ 1.20 (t,3H,J=6.5 Hz), 3.46–4.10 (m,2H,J=4 Hz) 5.07–5.26 (m,2H), 8.33 (bd s, 1H, exch.) which on prolonged storage (1 month) solidified to a white crystalline product; melting range 84°-6° C. (C$_6$H$_6$).

EXAMPLE 5

Preparation of 1,2,7,8-diepoxy-3,3,4,4,5,5,6,6-octafluorooctane:

To a solution of diazomethane (about 120 mmol.) in 200 ml of ether cooled to 5° C. in an ice bath, was added 10.0 g. (39.0 mmol.) of 2,2,3,3,4,4,5,5-octafluoro-1,6-hexanedialdehyde dropwise over 15 min. The solution was stirred for 30 min. and then allowed to stand unstoppered at room temperature for 16 hours at which time the yellow color indicative of diazomethane had been discharged. The solution was purged with nitrogen followed by evaporation in vacuo at ambient temperature to leave 11.0 g. of viscous, pale yellow oil. Distillation afforded 5.5 g. (49% by weight) of the title compound as a colorless liquid; boiling range 70°–75° C. (0.025 mm); $\eta_D^{26}$ 1.3622; nmr (CDCl$_3$) δ 3.04 (m,2H), 3.53 (m,1H); $\delta_{max}^{neat}$ 910 cm$^{-1}$.

EXAMPLE 6

Preparation of diethyl 3,3,4,4,5,5,6,6-octafluorodecane-2,8-dienedioate:

A mixture of 8.1 g. (2.3 mmol.) of (carbethoxymethylene)-triphenylphosphorane and 3.0 g. (1.2 mmol.) of 2,2,3,3,4,4,5,5-octafluoro-1,6-hexanedialdehyde in 40 ml. of toluene was heated at reflux for 18 hours under an atmosphere of nitrogen. The solution was chilled in ice, and the precipitated triphenylphosphine oxide was collected. The filtrate was diluted with 200 ml. of petroleum ether and a second crop of phosphine oxide removed. Evaporation of solvent under reduced pressure left an oil from which the residual phosphine oxide was removed by trituration with petroleum ether. Distillation of the evaporated petroleum ether supernatant gave 3.4 g. (74% by weight) of the title compound as a colorless liquid: boiling range 148°–53° C. (7.0 mm); $\eta_D^{25}$ 1.450.

It will be appreciated that other reagents conventionally employed in Wittig-type reactions may be substituted for the (carbethoxymethylene)-triphenylphosphorane, for example, methylenetriphenylphosphorane, ethylidenetriphenylphosphorane, diethyl cyanomethylphosphonate (Horner modification), and methoxymethyltriphenylphosphorane.

EXAMPLE 7

Preparation of 2,2,3,3,4,4,5,5-octafluoro-1,6-hexane-bis-2,4-dinitrophenylhydrazone:

2,2,3,3,4,4,5,5-octafluoro-1,6-hexanedialdehyde dihydrate 0.3 g. (about 1 mmol.) was dissolved in approximately 5 ml. of ethanol. About 9 ml. of a 0.25 molar solution of 2,4-dinitrophenylhydrazine in phosphoric acid-ethanol was added to the dialdehyde solution, and the mixture was warmed on a steam bath. A yellow solid separated which turned oily. Additional ethanol was added until a solid of good consistency was obtained in the hot solution. The solution was then cooled and the yellow solid collected, melting range 228°–230° C. (EtOH).

The foregoing procedure was repeated using 2-ethoxy-6-hydroxy-3,3,4,4,5,5-hexafluoropyran to yield 2,2,3,3,4,4-hexafluoro-1,5-pentane-bis-2,4-dinitrophenylhydrazone as a crystalline yellow solid, melting range 214°–216° C. (EtOH).

The importance of difunctional perfluorinated compounds has been extensively reviewed by I. L. Knunyants, L. Chih-Yuan, and V. V. Shokina, Rus. Chem. Revs., 32, p. 461 (1963). Consequently, the ready accessibility of the synthetically versatile perfluorinated dialdehydes and the derivatives thereof and of the intermediates of the subject invention should provide a valuable addition to the chemistry of highly fluorinated compounds.

Since certain changes may be made in the above compositions and processes without departing from the scope of the invention herein involved, it is intended that all matter contained in the above description should be interpreted as illustrative and not in a limiting sense.

What is claimed is:

1. A method which comprises reacting 1 equivalent of a compound of the formula ROOC—(CF$_2$)$_x$—COOR wherein R is alkyl having 1 to 4 carbon atoms and x is a positive integer 2 to 12 with about 1 to 1.5 equivalents of sodium bis-(2-methoxyethoxy)aluminum hydride at a temperature below about −40° C. in a solution of (a) toluene or benzene and (b) an alkyl ether having a freezing point below said reaction temperature and isolating the reaction product, said reaction product being a compound of the formula

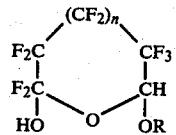

wherein n is 0 or 1 when said x is less then 4 and said reaction product being a compound of the formula

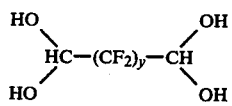

wherein y is 4 to 12 when x is at least 4.

2. A method as defined in claim 1 wherein said reaction temperature is between about −60° C. and −70° C.

3. A method as defined in claim 1 wherein said alkyl ether is tetrahydrofuran.

4. A method as defined in claim 1 wherein x is less than 4.

5. A method as defined in claim 4 wherein said reaction product is acidified and then reacted with a dehydrating agent in inert anhydrous organic solvent to yield the corresponding dialdehyde.

6. A method as defined in claim 5 wherein said dehydrating agent is phosphorus pentoxide.

7. A method as defined in claim 1 wherein x is at least 4.

8. A method as defined in claim 7 wherein said reaction product is reacted with a dehydrating agent in inert anhydrous organic solvent to yield the corresponding dialdehyde.

9. A method as defined in claim 8 wherein said dehydrating agent is phosphorus pentoxide.

* * * * *